(12) United States Patent
Hoescheler et al.

(10) Patent No.: US 7,264,665 B2
(45) Date of Patent: Sep. 4, 2007

(54) INERT DENTAL GLASS

(75) Inventors: Stefan Hoescheler, Herrsching (DE); Markus Mikulla, Andechs-Frieding (DE); Gabriele Rackelmann, Gilching (DE); Volker Bambach, Loerrach (DE)

(73) Assignee: 3M ESPE AG, Seefeld (DE)

( * ) Notice: Subject to any disclaimer, the term of this patent is extended or adjusted under 35 U.S.C. 154(b) by 0 days.

(21) Appl. No.: 10/451,222

(22) PCT Filed: Dec. 13, 2001

(86) PCT No.: PCT/EP01/14721

§ 371 (c)(1), (2), (4) Date: Dec. 8, 2003

(87) PCT Pub. No.: WO02/49581

PCT Pub. Date: Jun. 27, 2002

(65) Prior Publication Data

US 2004/0079258 A1  Apr. 29, 2004

(30) Foreign Application Priority Data

Dec. 20, 2000  (DE) ................ 100 63 939

(51) Int. Cl.
A61K 6/02  (2006.01)

(52) U.S. Cl. ............. 106/35; 523/116; 206/63.5; 206/219; 501/64; 501/73

(58) Field of Classification Search ........... 523/116; 206/63.5, 219; 106/35; 501/42, 44–52, 501/57–59, 63–68

See application file for complete search history.

(56) References Cited

U.S. PATENT DOCUMENTS

| | | | |
|---|---|---|---|
| 2,805,166 A | 9/1957 | Löffler | |
| 3,971,754 A * | 7/1976 | Jurecic | ........... 523/117 |
| 3,973,972 A | 8/1976 | Muller | |
| 4,024,070 A * | 5/1977 | Schuil | ........ 252/301.4 R |
| 4,143,018 A * | 3/1979 | Crisp et al. | ........... 524/559 |
| 4,360,605 A | 11/1982 | Schmitt et al. | |
| 4,376,835 A | 3/1983 | Schmitt et al. | |
| 4,527,979 A * | 7/1985 | McLean et al. | ........ 433/228.1 |
| 4,569,954 A | 2/1986 | Wilson et al. | |
| 4,727,283 A * | 2/1988 | van Kemenade et al. | ... 313/487 |
| 4,772,436 A | 9/1988 | Tyszblat | |
| 4,798,768 A * | 1/1989 | Oversluizen et al. | ........ 428/426 |
| 4,808,228 A * | 2/1989 | Randklev | ............. 106/35 |
| 4,900,697 A * | 2/1990 | Akahane et al. | ............. 501/57 |
| 4,927,866 A | 5/1990 | Purrmann et al. | |
| 5,051,453 A * | 9/1991 | Okabayashi et al. | ......... 523/116 |
| 5,179,135 A * | 1/1993 | Ellis et al. | ........... 523/116 |
| 5,250,585 A * | 10/1993 | Guggenberger et al. | ..... 523/116 |
| 5,384,293 A | 1/1995 | Omori et al. | |
| 5,520,922 A * | 5/1996 | Gasser et al. | ............. 424/422 |
| 5,641,347 A | 6/1997 | Grabowski et al. | |
| 5,849,068 A * | 12/1998 | Hofmann et al. | ............. 106/35 |
| 6,107,229 A * | 8/2000 | Luck et al. | ............. 501/151 |

FOREIGN PATENT DOCUMENTS

| | | |
|---|---|---|
| DE | 40 24 322 | 2/1992 |
| DE | 199 14 975 A1 | 10/2000 |
| EP | 0 230 113 A2 | 7/1987 |
| EP | 0 340 016 B1 | 1/1993 |
| EP | 0 783 872 A2 | 7/1997 |
| GB | 1316129 * | 4/1970 |
| GB | 1 316 129 | 5/1973 |
| GB | 2 291 060 | 1/1996 |
| JP | 58-2235 | 1/1983 |
| WO | WO 00/30953 | 6/2000 |

OTHER PUBLICATIONS

Neve, A.D. et al., *Clinical Materials* vol. 12, pp. 113-115 (1993).
Derwent Abstract Nr. 1994-362631[45].

* cited by examiner

Primary Examiner—C. Melissa Koslow
(74) Attorney, Agent, or Firm—Crowell & Moring LLP

(57) ABSTRACT

The invention relates to the use of ions of weakly basic oxides as linking ions for polyacids in cements, preferably polyelectrolyte cements. Suitable ions comprise elements of the scandium series, for example, $Sc^{3+}$, $Y^{3+}$, $La^{3+}$, $Ce^{4+}$ and all subsequent tri- and tetra-valent lanthanides and the ions $Mg^{2+}$, $Zn^{2+}$, $Ga^{2+}$, $In^{2+}$. The application of said ions permits a regulation of the cement reaction without surface treatment of the glass powder.

16 Claims, No Drawings

INERT DENTAL GLASS

This application claims the priority of International Application No. PCT/EP01/14721, filed Dec. 13, 2001 and German Application No. 100 63 939.9, filed Dec. 20, 2000, the disclosures of which are expressly incorporated by reference herein.

BACKGROUND AND SUMMARY OF THE INVENTION

The invention relates to the use of unreactive glasses in dental materials, in particular dental cements, preferably polyelectrolyte cements, which can be used without pretreatment of the glass powder surface.

In the dental sector, glasses are used in particular for filling materials and for the fixing cements and composites for crowns, bridges and inlays.

Reactive glasses, i.e. glasses which participate in a chemical reaction, are used in what are known as polyelectrolyte cements, in particular glass-ionomer cements.

Polyelectrolyte cements of this type generally comprise three constituents, namely a polyacid, in particular a substance which contains carbonic acid, preferably in liquid form, a glass powder and water. If the three components are combined and mixed with one another, a reaction occurs, so as to form a solid body which hardens over the course of time (cement reaction).

Various raw materials are used for the production of glasses which are used in particular in glass-ionomer cements. These raw materials are firstly oxides, such as $SiO_2$, $Al_2O_3$, CaO, fluorides, such as $CaF_2$, $SrF_2$, cryolite, hydroxides, such as $Al(OH)_3$, phosphates, such as $AlPO_4$, $P_2O_5$ or calcium phosphates. However, it is also possible to use silicates, such as mullite, or carbonates, such as $Na_2CO_3$, $CaCO_3$ or other natural mineral raw materials. In principle, it is also possible for all the raw materials to be used in a form which contains water of crystallization.

In dental glasses, a considerable proportion of the oxygen is often replaced by fluorine. This is indicated by adding the element symbol F for fluorine to the description of the glass system.

Accordingly, glasses for glass-ionomer cements can usually be assigned to one of the following systems, in which $P_2O_5$ and $Na_2O$ in some cases are only present in small amounts or are not present at all:

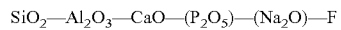

$SiO_2$—$Al_2O_3$—CaO—($P_2O_5$)—($Na_2O$)—F

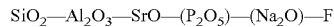

$SiO_2$—$Al_2O_3$—SrO—($P_2O_5$)—($Na_2O$)—F

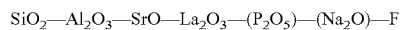

$SiO_2$—$Al_2O_3$—SrO—$La_2O_3$—($P_2O_5$)—($Na_2O$)—F

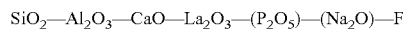

$SiO_2$—$Al_2O_3$—CaO—$La_2O_3$—($P_2O_5$)—($Na_2O$)—F

The glasses which are used in dental cements are generally fluoroaluminosilicate glasses. The solubility of the glass in acid is a precondition for it to be used as a constituent of a polyelectrolyte cement. An acid-soluble glass structure is formed if silicon is partially replaced by aluminum. However, silicon can only be replaced by aluminum if basic oxides are present, in order to create charge equalization for the trivalent aluminum ion at positions of the tetravalent silicon ion.

When the polyacids and water are added, the glass structure is broken up, and in particular the ions with network-modifying properties are at least partially released as what are known as crosslinker ions.

The crosslinking manifests itself in hardening of the cement which increases over the course of time. All at least divalent basic ions, but also $Al^{3+}$, are able to form polymeric structures of this type.

A distinction is usually drawn between the working time—the time during which the dentist is still able to work the still pasty cement material—and the hardening time—the time beyond which reworking is possible using rotating dental instruments.

It has been found that conventional glasses, which contain, for example, $Ca^{2+}$ and $Al^{3+}$ as crosslinker ions, in untreated form are too reactive and, on account of an excessive solubility, set too quickly with the polyacid, and consequently the dental cement which forms cannot reasonably be worked.

Although it is possible to slow the dissolution process by reducing the calcium content in the glass, it has been found that if the level of basic oxides, such as CaO or SrO, which can dissolve, is too low, the strength properties of the cement deteriorate as a result of insufficient availability of the ions. This means that the dentist has only a very short working time available to mix the filling material and apply it. At the same time, he has to accept the drawback of having to wait a very long time before he can start reworking the cement. This runs contrary to the demands which a dentist will impose on a dental cement.

The dentist usually requires a working time of from 1 to 4 min and a hardening time of from 5 to 8 min. The hardening time is usually determined according to ISO 9917 (First Edition) Part 7.3. The working time and the hardening time can be determined using a viscometer, as described in EP 0 023 013 A.

To achieve the desired working properties of the cement, i.e. to have sufficient working time and the shortest possible time to complete hardening, it is customary for the glass powders, after the milling process, to be subjected to surface treatment, as described, for example, in Clinical Materials 12, 113–115 (1993) or DE 29 29 121 A (EP 0 230 113 A). In this case, the glasses which react too quickly, on account of their composition, are adjusted to the desired level of reaction rate by reducing the levels of reactive ions at their surface.

EP 0 023 013 A describes the use of a calcium aluminum fluorosilicate glass powder for glass-ionomer cements to which further oxides may be added if they do not adversely affect the properties of the glass. According to the description, the surface of the glass has to be deactivated in order to obtain a glass which can be used for a dental cement. The deactivation represents a procedure whereby the reaction rate of a glass powder with an acid is delayed by a surface treatment, and in this way the desired working times of the cement are produced.

The deactivation of the surface can also be effected by means of other, relatively complex surface treatments, such as coating the surface, for example with a polymer.

In EP 0 023 013 A, this is achieved by means of a chemical treatment of the powder surface. The result is a cement with favorable working times combined, at the same time, with unchanged favorable mechanical characteristic data of the material.

However, this surface treatment of the glasses represents a complex process step.

Moreover, during the washing or conditioning processes, powder agglomeration may occur, having an adverse effect on the cement properties.

DE 38 06 448 A has disclosed a glass for a bone cement which comprises the elements Si, Al, Ca, Sr, F, Na and P and can be made visible to X-rays by the addition of $La_2O_3$. It is emphasized that the quantity of additives must not adversely affect the properties.

The glass powder described in DE 38 04 469 A is substantially free of alkali metal ions and alkaline-earth metal ions, with the exception of strontium which should be used in an amount from 15 to 40% by weight.

DE 20 65 824 B2 has described a fluoroaluminosilicate glass powder for self-hardening medical cements.

One object of the present invention is to provide a glass for a dental cement, in particular a reactive glass for a polyelectrolyte cement, which is simple to produce.

A further object can be considered to lie in that of directly using the glass immediately after the milling process without having to apply complex processes such as surface treatment, acid washing, coating and/or conditioning. The reactivity and therefore the working time and hardening time are then dependent only on the glass composition and the grain size distribution and are easy to produce reproducibly.

This object is achieved by a dental material containing a glass as described in the claims, and by the use of certain ions as crosslinker ions in a glass.

The invention also relates to hardenable materials, in particular cements, in particular polyelectrolyte cements, which contain these glasses.

In one embodiment, the invention relates to a process for producing a dental glass involving the steps a) providing oxidic substances, b) mixing the oxidic substances, c) melting the mixture from step b), d) quenching the molten material to form a solid, e) milling the solid from step d) to form a glass powder, the glass powder from step d) not being treated with acid before it is used in a dental cement.

In the context of the present invention, the term crosslinking is to be understood as meaning a reaction in which polyacids and at least divalent ions interact with one another in a chelate-forming reaction, preferably an acid-base-type reaction, leading to the formation of a polymeric network.

In the context of the present invention, the filling and fixing materials mentioned are to be understood as meaning substantially cements, and in particular polyelectrolyte cements. Accordingly, the glass described is preferably a reactive constituent rather than a conventional filler, unlike the glasses used in the composite sector, which are pure fillers and do not take part in a reaction.

Glasses for cements generally contain strongly basic ions, such as $Li^{2+}$, $Na^{2+}$, $K^+$, $Ca^{2+}$, $Sr^{2+}$, $Ba^{2+}$, $Zn^{2+}$. It has now been found that by completely or partially replacing the strongly basic ions with weakly basic ions, such as $Sc^{3+}$, $Y^{3+}$, $La^{3+}$, such as $Ce^{3+/4+}$ or other divalent, trivalent or tetravalent ions from the lanthanide series, and/or $Ga^{2+}$ or $In^{2+}$, glasses which set significantly more slowly with polyacids are obtained.

Surprisingly, such glasses can be used to produce dental cements which, substantially without a conventional surface treatment of the glass powders, have setting characteristics which are desired by the dentist. Furthermore, it has been found that the setting times can be adjusted within a wide range by means of the glass composition.

In this context, the invention has the following advantages:

As a result of the strongly basic ions, such as $Ca^{2+}$, $Sr^{2+}$, being replaced by the weakly basic ions $Sc^{3+}$, $Y^{3+}$, $La^{3+}$, $Ce^{4+/3+}$ and other divalent, trivalent and tetravalent ions from the lanthanide series in glasses which are used in dental cements, it is possible to achieve a controlled setting reaction of the dental cement, in particular of a glass-ionomer cement, without the glass having to be surface-treated, for example by acid washing and/or conditioning, before being used in the cement. In addition to simplified production, the advantage also resides in the improved reproducibility of the working and hardening times. Although these times are not adjusted by a surface treatment, the desired setting profile, namely a relatively rapid transition from a state in which the cement can still be worked to a state in which the hardening begins and useful working is no longer possible, is surprisingly achieved.

Amazingly, it has been discovered that dental materials or cement in which the abovementioned glasses are used have mechanical properties which are identical or even slightly improved compared to cements in which glasses whose reactivity has been reduced by acid washing are used.

Furthermore, it has been found that cements according to the invention are hydrolytically stable with respect to water.

These properties were found in particular in glasses which, in addition to Al and Si, contain only Y and/or La or contain only relatively small amounts of relatively strongly basic-reacting ions, such as $Ca^{2+}$ or $Sr^{2+}$, $Ba^{2+}$, $Li^+$, $Na^+$, $K^+$.

Furthermore, some of the oxygen can be replaced by fluorine, which on the one hand improves the meltability of the glass and on the other hand improves the setting properties of the cement and makes it possible to release fluoride ions for secondary caries prophylaxis.

Therefore, the previously known cement systems are expanded by the addition of the following systems.

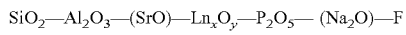

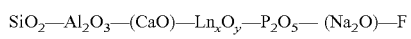

$Ln_xO_y$ stands for an oxide of the elements Sc, Y, La to Lu. x and y may adopt values of 1, 2 or 3 in this formula. The oxides which are inside parenthesis are used in only small amounts or are not used at all, since they would greatly accelerate the reaction. For example, DE 20 65 824 A describes a glass belonging to the system

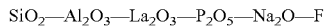

having an $Na_2O$ content of approx. 12% by weight.

Tests have shown that with this glass powder the setting rate with polyacids can only be brought into a manageable range after conditioning for several hours at 400° C. (cf. Comparative Example 4). This is presumably attributable to the high level of a strongly basic oxide, in this case $Na_2O$. A further drawback of a high $Na_2O$ content is the increased water solubility of the resulting cement.

Moreover, it has been found that the glasses described substantially do not have any phase-separation or crystallization effect within a wide range of compositions.

It is to be expected that the reproducibility of the setting rate of the cement containing the glasses will improve with clear glasses compared to segregated, i.e. opaque glasses, since their phase composition is not dependent on the cooling rate.

In addition to the standard components $SiO_2$, $Al_2O_3$, $P_2O_5$, and $Na_2O$, the glasses preferably mainly contain weakly basic and/or amphoteric-reacting ions, which act as crosslinker ions during the cement reaction.

Weakly basic trivalent and tetravalent ions are preferred, and the ions $Sc^{3+}$, $Y^{3+}$, $La^{3+}$, $Ce^{4+/3+}$ and all the following trivalent and tetravalent ions from the lanthanide series are particularly preferred.

Current teaching is that $Al^{3+}$ also belongs to the weakly basic or amphoteric-reacting ions. However, this ion adopts a special position among the glasses. Aluminum is primarily responsible for the solubility of the glass structure in acid and has only a secondary function as a crosslinker ion. In the glasses which are suitable for dental cements, aluminum, unlike the abovementioned trivalent and tetravalent ions, which function as network modifiers, acts as a network former.

The glasses used generally have a BET surface area of from 1 to 15 m$^2$/g, preferably 2 to 8 m$^2$/g.

Furthermore, the glasses have a mean grain size ($d_{50}$) of from 0.01 to 20 µm, preferably 1 to 5 µm.

It is preferable for 0 to 25% by weight of the oxygen in the glass used to be replaced by fluorine, particularly preferably from 8 to 18% by weight.

The $pK_B$ value is usually used to define the term basicity. A $pK_B$ of one can be taken as the limit between weakly and strongly basic. For example, the $pK_B$ of $Mg(OH)_2$ is given as one in R. C. Weast: CRC Handbook of Chemistry and Physics, while $Ca(OH)_2$ is classified as strongly basic, without being assigned a numerical value.

In the context of the present invention, oxides or hydroxides which only dissociate to a relatively minor extent in aqueous solutions are considered to be weakly basic.

In one embodiment, oxides with a $pK_B$ value of >1 are provided.

The following statements can be made in connection with the basicity:

The basicity increases from Sc through Y to La. La is to be classified as weakly basic compared to Sr, Ba or Na and K. At the same time, the basicity decreases again from La to Lu, and consequently the basicity of lutetium is approximately comparable to that of yttrium (lanthanide contraction).

Therefore, all oxides and hydroxides of the Sc series can be considered weakly basic in the context of present invention.

The elements from the 1st main group from Li through Cs and the elements from the second main group from Mg through Ba cannot be classified as weakly basic-reacting in the context of the present invention.

As has already been stated, it is assumed that, in addition to the base strength, the higher field strength of these ions also plays a certain role. This means that the ions described are anchored more strongly in the glass structure and are therefore dissolved out of it more slowly.

In the context of the present invention, the term polyacid is understood to mean a polyelectrolyte which includes a polymer with ionically dissociable groups, which may be substituents in the polymer chain and the number of which is so great that the polymers, at least in their (partially) dissociated form, are at least partially water-soluble. Substituents such as for example —COOH, —OH, —PO(OH)$_2$, —OPO(OH)$_2$, —SO$_2$(OH) are particularly suitable for this purpose. Organic polyacids (DE 20 61 513 A), such as polymers and copolymers of acrylic acid, methacrylic acid (EP 0 024 056 A), itaconic acid, maleic acid, citraconic acid, vinylphosphonic acid (EP 0 340 016 A; GB 22 91 060 A) are particularly preferred. In addition, if a plurality of polyelectrolytes are present, water-insoluble polyelectrolytes may also be present in the polyelectrolyte cement. The only condition is that at least one of the polyelectroytes be at least partially water-soluble.

The polyelectrolytes should be able to react with the glass component as part of a chelate-forming reaction and/or an acid-base reaction/neutralization reaction.

The polyelectrolyte cement contains the at least partially water-soluble polyelectrolyte, which can be converted into the solid state, preferably in an amount from 0.5 to 30% by weight, particularly preferably 2 to 25% by weight and very particularly preferably 5 to 20% by weight.

In the case of polyelectrolyte cements, the addition of chelating agents in order to establish a suitable setting characteristic is particularly important (DE 23 19 715 A). There are numerous compounds which are suitable for this purpose, in particular those which contain hydroxyl or carboxyl groups, or both, which form the chelating agents. Particularly good results have been achieved with tartaric acid or citric acid, in particular in an amount of 5% by weight. Adding the substance in the form of a metal chelate also has the desired effect.

The polyelectrolyte cements contain from 0 to 10, preferably 0 to 5% by weight of a compound of this type, preferably tartaric acid.

Furthermore, the polyelectrolyte cement may include auxiliaries, such as dyes, pigments, X-ray contrasting agents, flow improvers, thixotropic agents, polymer thickeners or stabilizers.

Examples of standard fillers for dental materials are glass and quartz powder, plastic powder, pyrogenic highly dispersed silicas and mixtures of these components.

Other suitable fillers may include: aluminum oxide, mineral powders, feldspars and kaolin.

These other additives are usually present in the polyelectroyte cements according to the invention in amounts of from 0 to 60% by weight.

The abovementioned fillers may also be rendered hydrophobic by means of a surface treatment with organosilanes or organosiloxanes or by etherification of hydroxyl groups to form alkoxy groups.

In principle, the glass composition which has been described is also suitable for use in monomer-modified cements.

It has proven favorable for the glass to contain from 20 to 70% by weight, preferably from 30 to 60% by weight, of weakly basic oxides.

The cement according to the invention may if appropriate contain strongly basic oxides in an amount in the range from 0 to 25% by weight, preferably in the range from 0 to 10% by weight.

The cement according to the invention preferably has a flexural strength in the region of at least 25 MPa to 35 Mpa, particularly preferably of greater than 45 MPa, measured in accordance with ISO 4049.

The working time of the cement, which is determined using a viscometer, is 1 to 4 min, particularly preferably 2 to 3 min. The hardening time is 3 to 10 min, particularly preferably 4 to 8 min.

Preferred compositions of the glasses are given below.

In addition to the abovementioned weakly basic oxides from the scandium series, the glasses may also contain oxides from transition groups 4 and 5. Also, the aluminum oxide may be partially or completely replaced by boron oxide or gallium oxide. The melting conditions can be positively influenced by the addition of oxides from the first main group, phosphate, and/or basic oxides from the second main group or ZnO.

The oxides which are separated from one another by "+" in the table, may, according to the invention, also be present just individually. The crucial factor is the corresponding proportion by weight which the group forms in the glass.

TABLE 1

| Oxide | Proportion |
|---|---|
| $Y_2O_3$ + $La_2O_3$ + other lanthanide oxides | 30 to 80% by weight, preferably 35 to 60% by weight |
| $B_2O_3$ + $Al_2O_3$ + $Ga_2O_3$ | 5 to 50% by weight, preferably 10 to 40% by weight, particularly preferably 15 to 35% by weight |
| $SiO_2$ + $GeO_2$ + SnO | 10 to 50% by weight, preferably 15 to 50% by weight |
| $P_2O_5$ | 0 to 15% by weight, preferably 0 to 10% by weight, particularly preferably 0 to 2% by weight |

TABLE 1-continued

| Oxide | Proportion |
|---|---|
| MgO + CaO + SrO + ZnO + BaO | 0 to 10% by weight, preferably 0 to 8% by weight, particularly preferably 0 to 5% by weight |
| $Li_2O$ + $Na_2O$ + $K_2O$ + $Rb_2O$ + $Cs_2O$ | 0 to 5% by weight, preferably 0 to 3% by weight, particularly preferably 0 to 2% by weight |
| $TiO_2$ + $ZrO_2$ + $HfO_2$ | 0 to 10% by weight, preferably 0 to 4% by weight |
| $V_2O_5$ + $Nb_2O_5$ + $Ta_2O_5$ | 0 to 10% by weight, preferably 0 to 4% by weight |

Instead of the "$Y_2O_3$+$La_2O_3$+other lanthanide oxides", it is also possible for $Sc_2O_3$ to be present in an amount of from 20 to 50% by weight, preferably from 20 to 30% by weight. Glass compositions in which $Sc_2O_3$ is present in addition to the above constituent in a relatively small amount are also included.

In one embodiment, the invention relates to a dental cement comprising:
  a) mineral solid in an amount of from 50 to 90% by weight;
  b) water in an amount of from 5 to 50% by weight; and
  c) polyacid in an amount of from 5 to 50% by weight.

Further, the $P_2O_5$ of Table 1 may be provided in an amount of from 0 to 18% by weight.

The invention is explained in more detail below with reference to a number of examples.

None of the glasses described in the examples was treated with an inorganic acid leading to a reduction in the number of reactive ions at the surface of the glasses (acid wash) before being reacted with a polyacid.

Production of the Glass:

Glasses of the following oxidic compositions (in % by weight) were melted at temperatures in the range from 1300 to 1600° C. over a period of 30 min to 5 h. With the exception of Comparative Example 4, the fluorine content in the starting batch was 12 to 14% by weight.

In Comparative Example 4, a glass was melted in accordance with DE 20 65 824 A1 using the following composition:

9.5 g of $SiO_2$, 10.0 g of $Al_2O_3$, 7.6 g of $Na_3AlF_6$, 9.4 g of $LaF_3$, 7.3 g of $AlPO_4$. The table gives the oxidic composition used in these examples.

TABLE 2

| | 1 | 2 | 3 | 4 | 5 | 6 | 7 | 8 | 9 | C1 | C2 | C3 | C4 | C5 | C6 | C7 |
|---|---|---|---|---|---|---|---|---|---|---|---|---|---|---|---|---|
| $SiO_2$ | 20 | 19 | 20 | 17 | 32 | 27 | 13 | 21 | 19 | 20 | 18 | 46 | 23 | 17 | 26 | 29 |
| $Sc_2O_3$ | | | | | | | | | | | | | | | | |
| $Y_2O_3$ | 36 | | 58 | | 20 | 41 | 50 | 46 | 49 | | | | | 48 | | 30 |
| $La_2O_3$ | | 48 | | 63 | 20 | | | | | 34 | | | 22.5 | | 23 | |
| CaO | | 7 | | | | | | | | 16 | 47 | | | 3 | 16 | |
| SrO | | | | | | | | | | | | 17 | | | | |
| $Al_2O_3$ | 44 | 26 | 22 | 20 | 28 | 32 | 37 | 28 | 26 | 29 | 34 | 35 | 36 | 26 | 30 | 27 |
| $P_2O_5$ | | | | | | | | 6 | | | | | 10 | | 5 | |
| ZrO2 | | | | | | | | | 5 | | | | | | | |
| $Na_2O$ | | 1 | | | | | | | | 1 | 1 | 2 | 8.5 | 6 | | 1 |
| Li2O | | | | | | | | | | | | | | | | 13 |

Milling 60 to 80 g of the glass granules obtained were dry-milled for 40 to 50 min a vibratory agate mill (produced by Siebtechnik, milling vessel 100 ml, 910 rpm). The glass powders obtained had a mean grain size in the range from 3 to 6 μm with a specific surface area of from 1.8 to 2.5 $m^2/g$.

EXAMPLE 6

Glass Example 6 was additionally wet-milled using a stirred ball mill. An aluminum oxide vessel (500 ml) was filled with 50 g of glass powder, 200 ml $H_2O$ and 100 g of zirconia balls (D=0.8 mm) and milling was carried out for 6 h using a perforated zirconia disk. The result was a mean grain size of 1.5 μm and a specific surface area of 10.5 $m^2$.

Cements

The cements were produced as a result of the glass powders obtained being mixed with polyacids. In this step, an approximately 45% strength polyacrylic acid (molecular weight 20,000 to 30,000), an approximately 45% strength polyacrylomaleic acid (molecular weight approx. 40,000 to 60,000) and an approximately 55% strength polyvinylphosphonic acid (molecular weight approximately 20,000) were used.

The setting was determined firstly in accordance with ISO 9917 and secondly using the viscometer described in EP 0 023 013 A1. In all cases, the test assembly ensured that the temperature of the specimens was controlled at 28° C. Flexural strengths were determined using the three-point bending test on 2×2×25 mm cement specimens in accordance with ISO 4049.

Results:

Cement 1:

Glass 1 was mixed both with a polyacrylic acid and a polyacrylomaleic acid with a P:F of 3:1.

TABLE 3

|  | Polyacrylic acid | Polyacrylomaleic acid |
|---|---|---|
| Viscometer (working time) | 3:30 | 3:50 |
| Viscometer (hardening time) | 9:10 | 9:00 |
| ISO 9117 | 8:30 | 7:30 |
| Flexural strength [Mpa] | 39.4 | 31.8 |

Cement 6:

Glass 6 was reacted with polyacrylic acid (45% strength) with a P:F of 2.0:1.

TABLE 4

|  | Dry milling | Stirred-ball milling |
|---|---|---|
| Viscometer (working time) | 5:00 | 2:10 |
| Viscometer (hardening time) | 12:00 | 7:45 |
| ISO 9117 | 10:30 | 4:00 |
| Flexural strength | 27.9 MPa | 41.5 MPa |

Glass C6:

The glass, in one case untreated and in one case after conditioning for 6 hours at 400° C. in a circulating air oven (produced by Heraeus), was reacted with polyacrylic acid.

TABLE 5

|  | untreated | conditioned |
|---|---|---|
| Viscometer (working time) | not determinable | 1:50 |
| Viscometer (hardening time) |  | 5:20 |
| ISO 9117 | not determinable | 5:00 |
| Flexural strength | not determinable | 37.4 MPa |

Further Cement Examples:

TABLE 6

| Glass | 2 | 3 | 4 | 5 | 7 | 8 | 9 | C1 | C2 | C3 | C4 | C5 | C7 |
|---|---|---|---|---|---|---|---|---|---|---|---|---|---|
| P:F | 3:1 | 3:1 | 3:1 | 3:1 | 3.5:1 | 4:1 | 4:1 | 3:1 | 3:1 | 3:1 | 3:1 | 4:1 | 4:1 |
| Viscometer (working time) | 1:30 | 2:50 | 2:40 | 3:20 | 4:00 | 3:50 | 2:50 | 0:45 | <1:0 | <1:0 | <1:0 | <1:0 | <1:0 |
| Viscometer (hardening time) | 3:50 | 8:20 | 5:20 | 7:40 | 9:10 | 8:50 | 6:45 | 1:30 | <1:0 | <1:0 | <1:0 | <1:0 | <1:0 |
| ISO 9917 | 4:00 | 7:15 |  | 5:00 | 8:30 | 7:40 | 6:00 | 1:00 | <1:0 | <1:0 | <1:0 | <1:0 | <1:0 |
| Three-point flexural strength | 37.4 | 41.6 |  | 34.8 | 35.6 | 32.9 | 43.9 | — | — | — | — | — | — |

The setting times determined for the cements obtained in Examples 1 to 9 are all within the preferred range, with the exception of Glass 6, which was only dry-milled.

The cement in accordance with Comparative Example 1 sets too quickly, presumably on account of the high Ca content. With the cements according to Comparative Examples 2 and 3, measurement was no longer possible, on account of setting taking place too quickly.

With the measurements using the viscometer, the first time corresponds to the working time and the second time corresponds to the hardening time. The times given are in minutes. The P:F ratio is given as a weight ratio.

The cements according to the invention are usually marketed packaged in vessels. In this context, it should be ensured that the individual components of the cement are in a form which is such that there is no undesirable reaction before they arrive at their intended use. The vessels usually have at least two chambers which are separated from one another. Examples of suitable vessels are described in WO 00/30953 A or EP 0 783 872 A.

Suitable vessels are mixing capsules and closeable boxlike hollow bodies, such as screw-capped jars. In one embodiment, the vessel has at least two compartments. In such an arrangement, the free-flowing constituents may be separated from the solid constituents of the cement. Depending on the particular application, the cements may also be packaged in capsules.

The invention claimed is:

1. A dental cement comprising a dental glass comprising:

| Oxide | Proportion |
|---|---|
| a member selected from the group consisting of $Y_2O_3$, $La_2O_3$, $Gd_2O_3$, $Yb_2O_3$, and $Lu_2O_3$ or $Sc_2O_3$ by itself | [[30]] 35 to 60% by weight 20 to 50% by weight |
| $Al_2O_3$ | 15 to 40% by weight |
| $SiO_2$ | 15 to 50% by weight |
| $P_2O_5$ | 0 to 2% by weight |
| at least one of MgO, CaO, SrO, ZnO, and BaO | 0 to 8% by weight |
| at least one of $Li_2O$, $Na_2O$, $K_2O$, $Rb_2O$, and $Cs_2O$ | 0 to 2% by weight |
| at least one of $TiO_2$, $ZrO_2$, and $HfO_2$ | 0 to 4% by weight |
| at least one of $V_2O_5$, $Nb_2O_5$, and $Ta_2O_5$ | 0 to 4% by weight |

2. The dental cement of claim 1, further comprising:
   A) mineral solid in an amount of 50 to 90% by weight,
   B) water in an amount from 5 to 50% by weight and C) polyacid in an amount from 5 to 50% by weight, wherein the mineral solid comprises the dental glass.

3. The dental cement as claimed in claim 1, wherein the dental material comprises a three-component system.

4. The dental cement as claimed in claim 1, wherein fluorine replaces from 0 to 25% by weight of the oxygen in the dental glass.

5. The dental cement as claimed in claim 1, wherein the dental glass is in powder form with a specific BET surface area of 1 to 15 $m^2/g$.

6. The dental cement as claimed in claim 1, wherein the dental glass has a mean grain size in a range from 0.01 to 10 µm.

7. The dental cement as claimed in claim 1, wherein the surface of the dental glass has not been washed with acid, surface coated or conditioned in order to adjust the setting time.

8. The dental cement as claimed in claim 1, further comprising at least one filler from 0 to 60% by weight in component A).

9. The dental cement as claimed in claim 8, wherein said at least one filler is selected from the group consisting of quartz, glasses, aluminum oxide, mineral powders, feldspars, kaolin, and plastic powder.

10. The dental cement as claimed in claim 2, wherein the dental cement has a flexural strength of at least 25 MPa when determined in accordance with ISO 4049.

11. A method of producing a dental cement as described in claim 2, wherein the surface of the dental glass has not been washed with acid, surface coated, or conditioned, wherein the dental cement is a polyelectrolyte cement and wherein the components of the dental glass are melted to form a dental glass, comprising the step of mixing the mineral solid, water and polyacid to form the dental cement.

12. A process for producing the dental cement according to claim 1, comprising
reacting a polyacid with weakly basic reacting oxides present in the glass where the glass has not been surface treated.

13. The process as claimed in claim 12, wherein the dental cement is a polyelectrolyte cement.

14. A vessel, comprising a dental cement, wherein the dental cement comprises a dental glass comprising:

| Oxide | Proportion |
|---|---|
| a member selected from the group consisting of $Y_2O_3$, $La_2O_3$, $Gd_2O_3$, $Yb_2O_3$, and $Lu_2O_3$ or $Sc_2O_3$ by itself | 35 to 60% by weight 20 to 50% by weight |
| $Al_2O_3$ | 15 to 40% by weight |
| $SiO_2$ | 15 to 50% by weight |
| $P_2O_5$ | 0 to 2% by weight |
| at least one of MgO, CaO, SrO, ZnO, and BaO | 0 to 8% by weight |
| at least one of $Li_2O$, $Na_2O$, $K_2O$, $Rb_2O$, and $Cs_2O$ | 0 to 2% by weight |
| at least one of $TiO_2$, $ZrO_2$, and $HfO_2$ | 0 to 4% by weight |
| at least one of $V_2O_5$, $Nb_2O_5$, and $Ta_2O_5$ | 0 to 4% by weight | and comprising
A) mineral solid in an amount of 50 to 90% by weight,
B) water in an amount from 5 to 50% by weight and
C) polyacid in an amount from 5 to 50% by weight, wherein the mineral solid comprises the dental glass, and
additional constituents;
wherein the vessel comprises at least two compartments; and
wherein free-flowing constituents are separated from solid constituents.

15. A vessel, comprising a dental cement according to claim 1, wherein the vessel comprises at least two chambers wherein components capable of flowing are separated from the solid components in the at least two chambers.

16. The vessel as claimed in claim 15, wherein the vessel is in the form of a mixing capsule.

* * * * *

UNITED STATES PATENT AND TRADEMARK OFFICE
CERTIFICATE OF CORRECTION

PATENT NO. : 7,264,665 B2  Page 1 of 1
APPLICATION NO. : 10/451222
DATED : September 4, 2007
INVENTOR(S) : Stefan Hoescheler It is certified that error appears in the above-identified patent and that said Letters Patent is hereby corrected as shown below:

Column 3
Line 46, delete "$Li^{2+}$, $Na^{2+}$," and insert -- $Li^+$, $Na^+$, --, therefor.

Column 4
Line 20, delete "$Ba^2+$," and insert -- $Ba^{2+}$, --, therefor.

Column 5
Line 60, delete "polyelectroytes" and insert -- polyelectrolytes --, therefor.

Column 6
Lines 27-28, delete "polyelectroyte" and insert -- polyelectrolyte --, therefor.

Column 8
In (Table 2), line 9, in (Col. 1), delete "ZrO2" and insert -- $ZrO_2$ --, therefor.
In (Table 2), line 11, in (Col. 1), delete "Li2O" and insert -- $Li_2O$ --, therefor.

Signed and Sealed this

Thirteenth Day of May, 2008

JON W. DUDAS
*Director of the United States Patent and Trademark Office*